US00PP24634P3

(12) United States Plant Patent
Coiner

(10) Patent No.: US PP24,634 P3
(45) Date of Patent: Jul. 15, 2014

(54) HYBRID TEA ROSE PLANT NAMED 'FLIRTY GIRL'

(50) Latin Name: *Rosa hybrida*
Varietal Denomination: Flirty Girl

(76) Inventor: James W. Coiner, Covina, CA (US)

( * ) Notice: Subject to any disclaimer, the term of this patent is extended or adjusted under 35 U.S.C. 154(b) by 94 days.

(21) Appl. No.: 13/573,348

(22) Filed: Sep. 10, 2012

(65) Prior Publication Data

US 2014/0075612 P1 Mar. 13, 2014

(51) Int. Cl.
*A01H 5/00* (2006.01)

(52) U.S. Cl.
USPC ..... Plt./131; Plt./130; Plt./132; Plt./139

(58) Field of Classification Search
USPC ..... Plt./130, 131, 132, 139
See application file for complete search history.

*Primary Examiner* — Susan McCormick Ewoldt
(74) *Attorney, Agent, or Firm* — Christie, Parker & Hale, LLP

(57) ABSTRACT

A new variety of Hybrid Tea rose suitable for garden decoration, having flowers of pink and light yellow coloration.

1 Drawing Sheet

Classification: The present invention relates to a new *Rosa hybrida* plant.

Variety denomination: The new plant has the varietal denomination 'FLIRTY GIRL'.

BACKGROUND OF THE INVENTION

This invention relates to a new and distinct variety of Hybrid Tea Rose. It has as its seed parent the variety known as unknown seedling and as its pollen parent the variety known as unknown seedling.

SUMMARY OF THE INVENTION

Among the features which distinguish the new variety from other presently available and commercial rose cultivars known to the inventor are the following combination of characteristics: The plant has a compact upright growing plant growth habit and is suitable for outdoor garden decoration.

Asexual reproduction of the new variety by budding as performed in Kern County shows that the foregoing and other distinguishing characteristics come true to form and are established and transmitted through succeeding asexual propagations. 'Flirty Girl' may be asexually propagated by cuttings, budding and grafting. The budding and grafting successfully occurred on the plant/rootstock *Rosa hybrida* cv. 'Dr. Huey' (unpatented).

COMPARISON WITH THE CLOSEST COMMERCIALLY AVAILABLE CULTIVAR

The new variety may be distinguished from its closest commercially available cultivar, 'Double Delight' (U.S. Pat. No. 3,847) by the following combination of characteristics: lighter color red on the edges of the blooms, and not as fragrant, the foilage is a much darker green.

BRIEF DESCRIPTION OF ILLUSTRATION

The accompanying photograph (FIG. 1) illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 2 year-old rose plants of the new variety grown outdoors in Wasco, Calif. in the month of October. Phenotypic expression may vary with environmental, cultural and climatic conditions, as well as differences in conditions of light and soil.

FLOWER

The new variety sometimes usually bears its flowers singly. Flowers are borne in regular clusters on long stems (about 50 cm to 55 cm). Outdoors, the plant blooms abundantly during the growing season. The flowers have a slight fruity fragrance.

BUD

The peduncle is about 50 mm to about 55 mm in length, average in diameter, and sometimes usually erect stiff. It is usually smooth, with few stipitate glands, and some hairs and prickles. Peduncle color is near between 14b and 14c.

Before the calyx breaks, the bud is about 2.5 cm to about 3 cm in diameter at the widest point, about 3 cm to about 3.5 cm in length, and globular in shape with a conspicuous neck. The surface of the bud bears foliaceous appendages stipitate glands and glandular bloom, usually with slender cut bristle-like foliaceous parts extending beyond the tip of the bud about ¼ of its length. Bud color is near 74b and 74c at tip, and 158c and 158c, in the center, and 20b and 20c, at the base.

The sepals are about 10 cm to about 11 cm in length and about 7 cm to about 8 cm in width at the widest point. The outer surface color of the sepal is near between 138b and 138c. The inner surface color of the sepal is near between 144a and 144b and covered edged with fine wooly tomentum; sepal margins are lined with some stipitate glands and hairs.

The receptacle of the flower is of somewhat short to medium length (about 10 cm to about 11 cm). The receptacle is funnel shaped in form. Its surface is smooth. The receptacle color is near between 139c and 139d.

As the petals open (after the calyx breaks), the bud is about 25 mm to about 30 mm in diameter at the widest point, about 40 mm to about 50 mm in length, and ovoid in form. The color when sepals first divide bud color is 158d often with 74b and 74c on the edges.

BLOOM

When fully open, the bloom ranges from about 12 cm to about 13 cm in diameter. Petalage is double with about 30 to 35 petals and about 3 to 7 petaloids irregularly arranged. When partially open, the bloom form is high centered, and the petals are tightly spiraled to undulated with petal edges very rolled outward. When fully open, the bloom form is full, and the petals are loosely cupped to flat to undulated with petal edges rolled outward.

PETALS

The substance of the petals is thick and leathery, with upper surfaces shiny, and under surfaces slight velvety. The petals are about 4 cm to about 4.5 cm in length and about 4.5 cm to about 5 cm in width at the widest point. Petal margins are somewhat serrate.

The outer petals are nearly oval in shape with apexes somewhat rounded, sometimes notched with one to two notches.

The inner petals are nearly oval in shape with apexes somewhat rounded sometimes notched with one to two notches.

NEWLY OPENED FLOWER

The upper sides of the petals are near 74b and 74c on the outer edges changing to 158c and 158d in the center, and to 20b at inner bottom.

The under and upper surface color of the petaloids are similar in coloration to the upper and under surfaces of the intermediate and inner petals.

The general tonality of the newly opened flower is near between 74b and 74c.

THREE-DAY OLD FLOWER

The upper sides of the petals are near 74b and 74c on the outer edges changing to 158c and 158d in the center, and to 20b at inner bottom.

The under and upper surface color of the petaloids are similar in coloration to the upper and under surfaces of the intermediate and inner petals.

The general tonality of the newly opened flower is near between 74b and 74c.

The under and upper surface color of the petaloids are similar in coloration to the upper and under surfaces of the intermediate and inner petals.

The general tonality of the three-day-old flower is near between 74b and 74c, little change.

On the spent bloom, the petals usually drop off cleanly in October in Wasco, Calif.

Blooms on the bush growing outdoors generally last about four to five days. Cut roses from plants grown outdoors and kept at normal indoor living temperatures generally last about five to seven days.

MALE REPRODUCTIVE ORGANS

Stamens are average in number (average about 60-70) and are arranged regularly; a few are mixed with petaloids or tucked in the calyx. The filaments are medium length (about 8 mm to about 9 mm) most with anthers. Filaments are near between 12b and 12c in color. The anthers are medium for the class and all open approximately at the same time. Anther color is near between 15c and 15d. Pollen is moderate to abundant and near 22b and 22c in color.

FEMALE REPRODUCTIVE ORGANS

Pistils vary in number (average about 35-40). The styles are thin, average in length (about 2 mm to about 2.5 mm). Stigma color is near between and style color is near between 16b and 16c. Ovaries are usually enclosed in the calyx, although few may protrude from the calyx.

Hips have not been observed on this variety when grown in Wasco, Calif.

FOILAGE

The compound leaves are usually comprised of five to seven leaflets and are borne to normal quantities. The five-leaflet leaves are about 45 mm to about 50 mm in length and about 30 mm to about 35 mm in width at the widest point, leathery in texture, and very glossy, rugose in finish. The terminal leaflets are about 20 mm to about 25 mm in length and about 15 mm to about 18 mm in width at the widest point, shaped oblong with round obtuse bases. Their margins are usually serrate.

The upper and under surface color of the mature leaf is near between 141c and 141d. The under surface color of the mature leaf is near between 146b and 146c. The upper and under surface color of the young leaf is near between 53a and 53b.

The rachis is average in caliper and smooth. The upper side is moderately grooved with few hairs. The rachis color is near between 147c and 147d.

The stipules are about 15 mm to about 17 mm in length and somewhat narrow width.

The petiole is average in caliper and somewhat rough. The upper side is deeply to moderately shallowly grooved with few hairs and stipitate glands and prickles on the edges of the grooves. The under side of the rachis is moderately rough with few hairs and stipitate glands and medium prickles. The petiole color is near between 147c and 147d.

The plant displays an average degree of resistance to powdery mildew and rust as compared to other commercial varieties grown under comparable conditions in Wasco, Calif. The plant's winter hardiness and drought/heat tolerance are yet to be determined.

GROWTH

The plant has an upright growth habit (about 150 cm to about 170 cm in height and about 70 cm to about 80 cm spread at the widest point), with full branching. It displays vigorous growth and the canes are of medium caliper for the class.

The color of the major stems is near between 146a and 146b. They bear few prickles that are about 10 mm to about 12 mm in length. The large prickles are hooked slightly downward; prickle color is near between 168c and 168d. The major stem bears few small prickles of similar shape and coloration and which are near between 178b and 178c in color.

The color of the branches is near between 146c and 146d. They bear few prickles which are of similar size and shape to the large prickles on the major stems; prickle color is near between 178a and 176b.

The color of the new shoots is near between 146c and 146d. They bear few prickles which are of similar size and shape to the large prickles on the major stems; prickle color is near between 178b and 178c.

I claim:

1. A new and distinct Hybrid Tea rose plant of the variety substantially as described and illustrated herein.

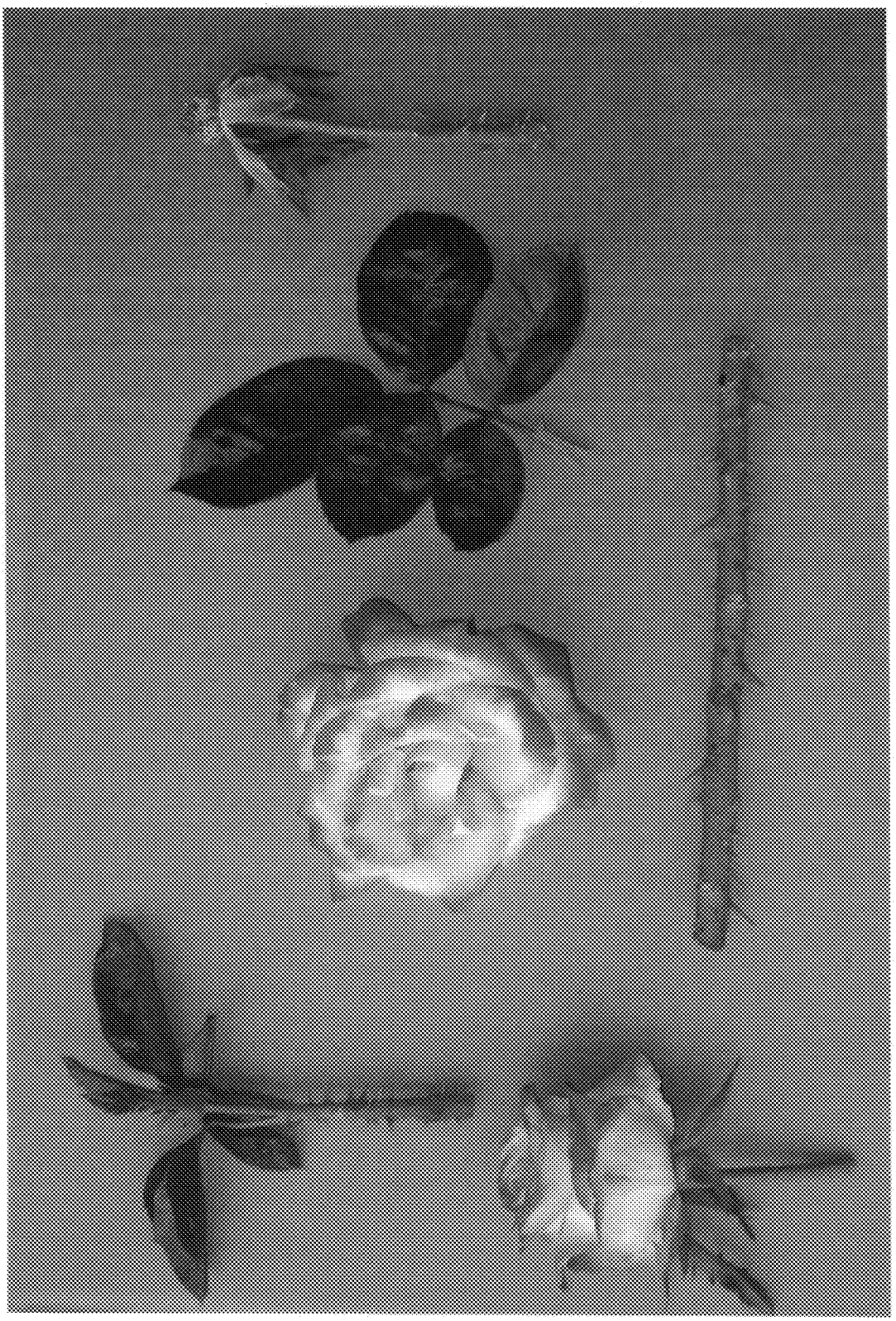

* * * * *